(12) United States Patent
Kim et al.

(10) Patent No.: US 6,352,522 B1
(45) Date of Patent: *Mar. 5, 2002

(54) DISPOSABLE SYRINGE ASSEMBLY

(75) Inventors: Han Wook Kim; Chung Sil Lee; Hyung Lee, II, all of Seoul (KR)

(73) Assignee: Boo Yoon Tech, Inc., Seoul (KR)

( * ) Notice: This patent issued on a continued prosecution application filed under 37 CFR 1.53(d), and is subject to the twenty year patent term provisions of 35 U.S.C. 154(a)(2).

Subject to any disclaimer, the term of this patent is extended or adjusted under 35 U.S.C. 154(b) by 0 days.

(21) Appl. No.: 09/380,339

(22) PCT Filed: Dec. 13, 1997

(86) PCT No.: PCT/KR97/00264

§ 371 Date: Sep. 2, 1999

§ 102(e) Date: Sep. 2, 1999

(87) PCT Pub. No.: WO98/25660

PCT Pub. Date: Jun. 18, 1998

(30) Foreign Application Priority Data

Dec. 13, 1996 (KR) .............................. 96-48551

(51) Int. Cl.$^7$ ................................ A61M 5/24
(52) U.S. Cl. ................ 604/201; 604/232; 604/200
(58) Field of Search ................ 604/187, 192, 604/197, 200, 201–202, 218, 227–228, 232, 243–244

(56) References Cited

U.S. PATENT DOCUMENTS

| | | | | |
|---|---|---|---|---|
| 3,967,759 A | * | 7/1976 | Baldwin et al. | 222/145 |
| 4,303,069 A | * | 12/1981 | Cohen | 128/218 |
| 4,723,945 A | * | 2/1988 | Theiling | 604/232 |
| 5,122,117 A | * | 6/1992 | Haber et al. | 604/90 |
| 5,554,125 A | * | 9/1996 | Reynolds | 604/187 |
| 5,688,250 A | * | 11/1997 | Naganuma | 604/200 |
| 5,728,076 A | * | 3/1998 | Loos et al. | 604/232 |
| 5,833,669 A | * | 11/1998 | Wyrick | 604/234 |
| 6,068,616 A | * | 5/2000 | Janus | 604/240 |

\* cited by examiner

*Primary Examiner*—Sharon Kennedy
*Assistant Examiner*—Catherine Serke
(74) *Attorney, Agent, or Firm*—Finnegan, Henderson, Farabow, Garrett & Dunner, LLP (57) ABSTRACT

This design relates to a disposable syringe assembly with possibly small-sized finger grip, while any part of the syringe is applicable for injection and medicaments are pre-filled for quick use. In particular, the device of this design relates to a disposable syringe assembly, comprising: plunger (40) having an oval shape at the front end and plunger tip (41) at the terminal end; plunger rod (50) having a disc (53) at the end of a screw (51) combined with a plunger tip (41) of said plunger (40); glass tube (10) where one side is clogged by the plunger (40), the other side is sealed by a rubber seal (21) and aluminum cap (25), and its outer diameter coincides with that of projection (17*a*) clogged by said plunger (40); finger grip (30) having a groove (33) to insert the projection (17*a*) of said glass tube (10) and a ring (31) as well; needle hub (60) having the inserted part sealed by a rubber seal (21) and aluminum cap (25) into said glass tube (10) as well as a needle hub mount (63) to hold two annular projections (67*a*, 67*b*) and needle (71) within an internal diameter; needle shield (73) being attached to a needle mount (63) of said needle hub (60). Since the finger grip has also a hexagonal shape, the device of this design has several advantages in that a) any part of syringe grip may be applicable prior to use, b) by preventing the displacement of a plunger before or after use, the discharge of contents during use or storage may be prevented, and c) the device cannot be refilled after use. Further, the device of this design is very useful in achieving the innate object of a disposable syringe assembly by solving the full administration of pharmaceuticals. Further, by detachedly mounting the rubber seal and aluminum cap, the device of this design can effectively prevent the mixing of aluminum particles into the medicaments.

4 Claims, 7 Drawing Sheets fig.1 fig.2 fig.3 fig.4 fig.5 fig.6a fig.6b fig.7 fig.8

DISPOSABLE SYRINGE ASSEMBLY

BACKGROUND OF THE INVENTION

1. Field of the Invention

This design relates to a disposable syringe assembly and more particularly, to a disposable syringe assembly with possibly small-sized finger grip, while any part of the syringe is applicable for injection and medicaments are pre-filled for quick use.

2. Description of the Prior Art

Currently, disposal pre-filled syringe assemblies for dispensing parenteral pharmaceuticals by injection are not new per se. Many syringe assemblies have been proposed which employ a glass tube filled with the desired medicaments.

The conventional disposable syringe assembly structure is constructed in such a manner that at one end of the glass tube is a plunger tip which functions as a seal for medicaments, while at the other end of the glass tube is a seal in the form of an elastomeric disk held in place by a plastic or metal rod.

Further, the needle design which is generally used with disposable pre-filled syringe assemblies involves the use of a double ended needle assembly which is attached to the sealed end of the glass tube in a first position where the needle is aligned with the needle hub but not penetrating the seal.

The needle then is movable to a second position whereby the interiorly pointing end of the needle penetrates the seal and provides assess to the contents. The other end of the needle which is, of course, the end through which the medicine is administered to the patient, is covered by a needle shield.

Particularly, none of the prior art provides a compact assembly which is provided with a functional locking mechanism to prevent inadvertent movement or damage to seals at either end of the pre-filled containe.

Furthermore, a rubber portion is liable to be depressed during the sealing of an aluminum cap and then, aluminum particles are attached to the rubber portion.

Finally, the finger grip structure has recognized some disadvantage in that fingers should accurately be folded on two protruded support humps, when administered.

SUMMARY OF THE INVENTION

Accordingly, to overcome the aforementioned problems, it is an object of this design to a) decrease the volume of a finger grip to a great extent, b) freely use any parts of the syringe assembly, c) prevent the displacement of a plunger before or after using the syringe assembly, and d) administer a full amount of medicaments.

Further, another object of this design is to provide a disposable syringe assembly which can be safely stored or transported from any outer impact and cannot be re-filled for use, thus achieving the innate object of a disposable syringe assembly.

DETAILED DESCRIPTION OF THE INVENTION

To achieve the above object, the device of this designed related to a disposable syringe assembly, comprising:

plunger 40 having an oval shape at the front end and plunger tip 41 at the terminal end;

plunger rod 50 having a disc 53 at the end of a screw 51 combined with a plunger tip 41 of said plunger 40;

glass tube 10 where one side is clogged by the plunger 40, the other side is sealed by a rubber seal 21 and aluminum cap 25, and its outer diameter coincides with that of projection 17a clogged by said plunger 40;

finger grip 30 having a groove 33 to insert the projection 17a of said glass tube 10 and a ring 31 as well;

needle hub 60 having the inserted part sealed by a rubber seal 21 and aluminum cap 25 into said glass tube 10 as well as a needle hub mount 63 to hold two annular projections 67a, 67b and needle 71 within an internal diameter;

needle shield 73 being attached to a needle mount 63 of said needle hub 60.

This design is explained in more detail as set forth hereunder by referring to the accompanying drawings.

Figure 1:
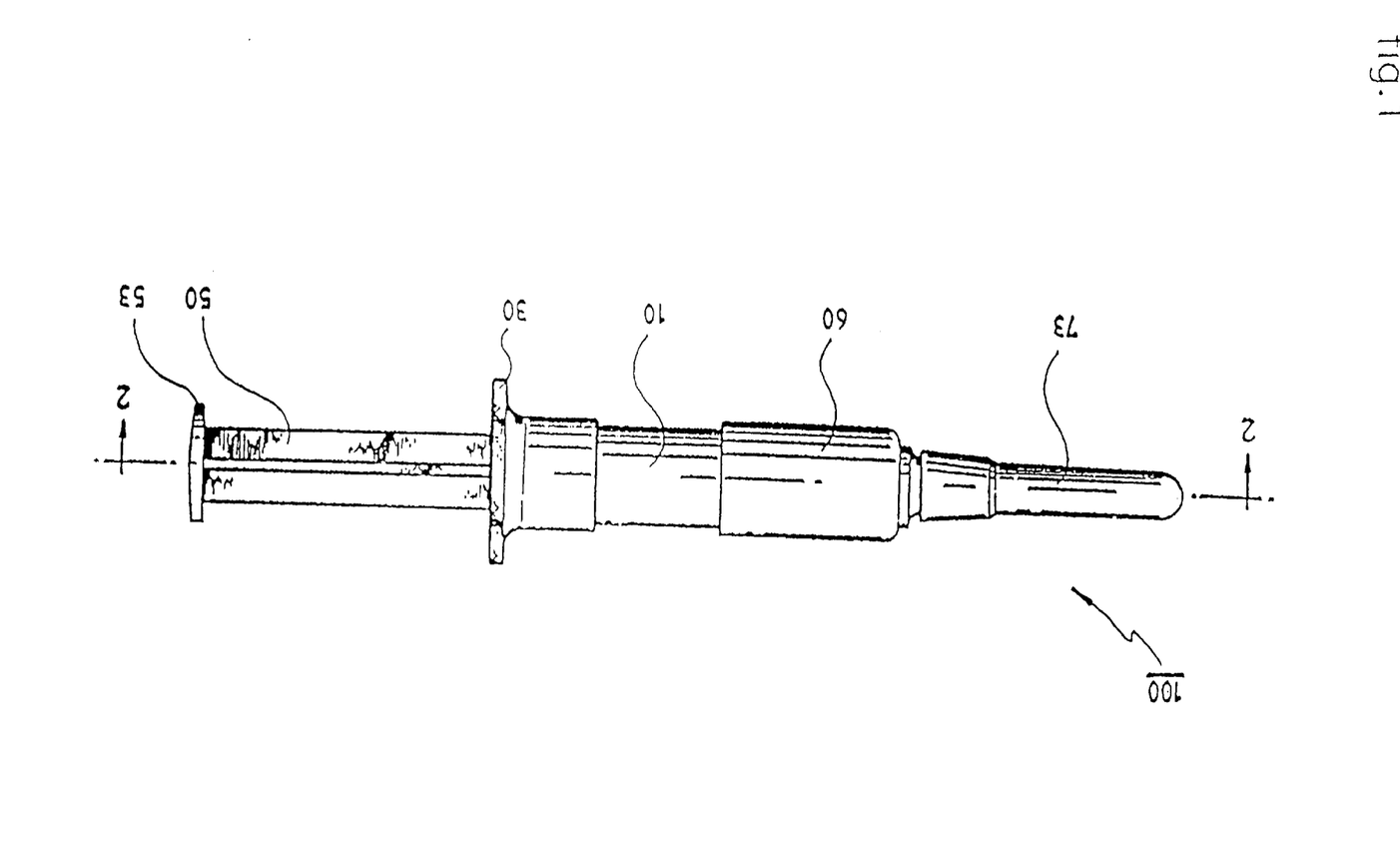
FIG. 1 is an elevational view of this design.
Figure 2:
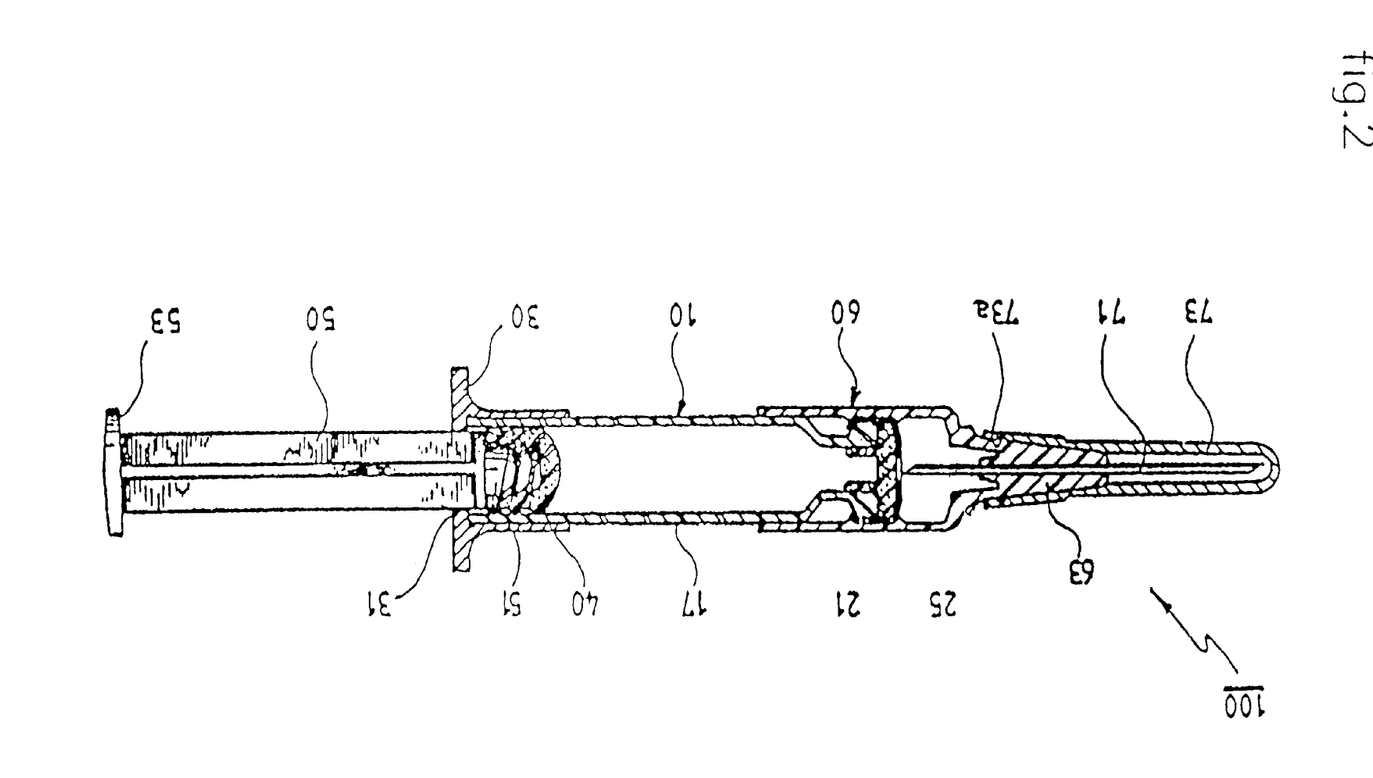
FIG. 2 is a cross-sectional view of this design.
Figure 3:
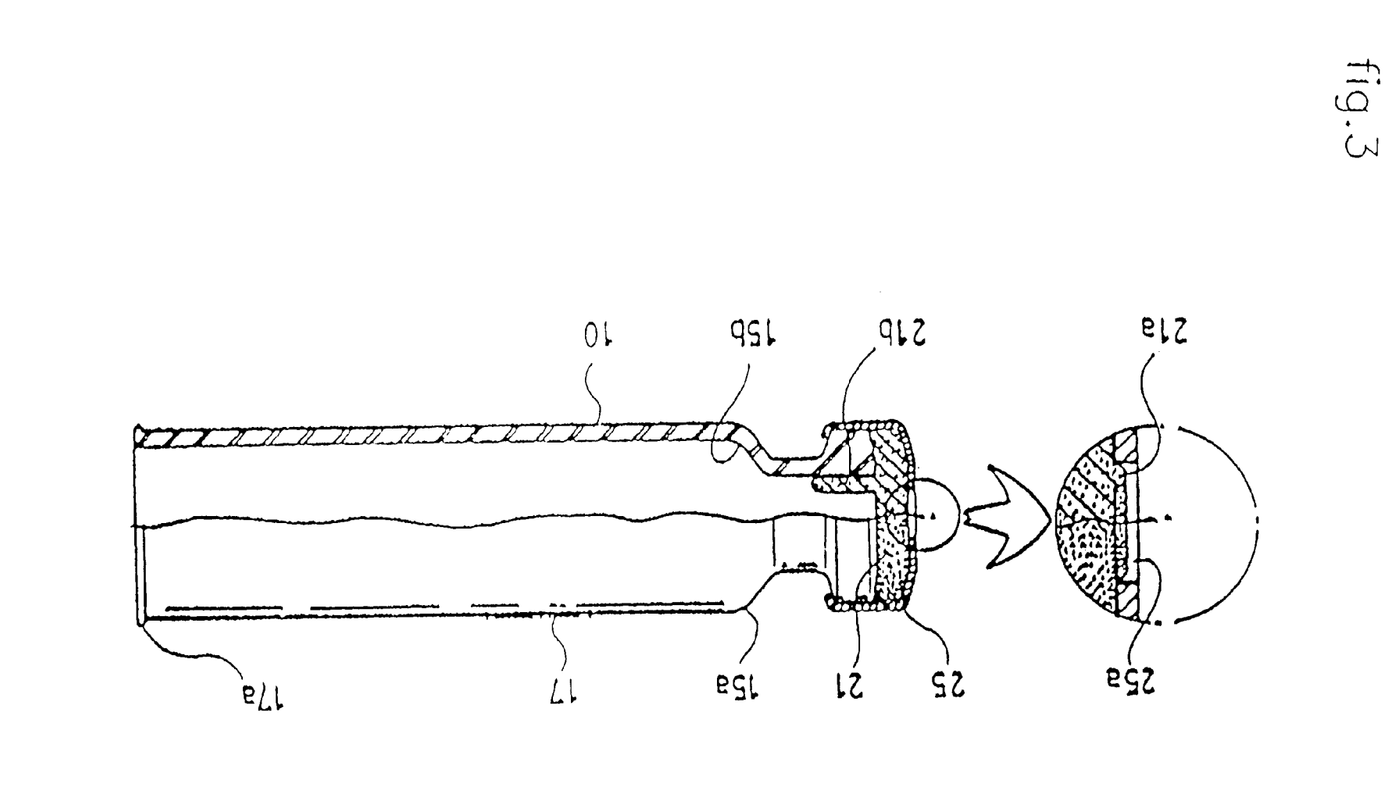
FIG. 3 is a partial cross-sectional view of the glass tube sealed with aluminum cap of this design.
Figure 4:
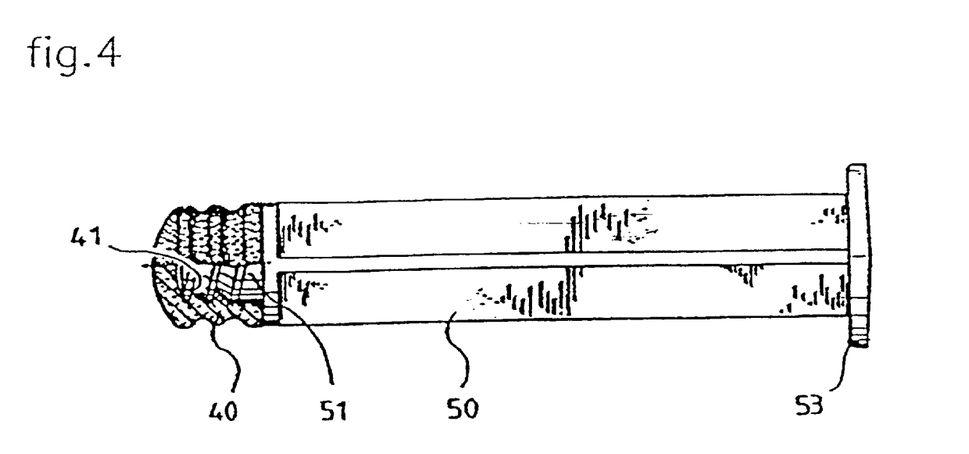
FIG. 4 is a cross-sectional view where a plunger rod is mounted on a plunger tip of this design.
Figure 5:
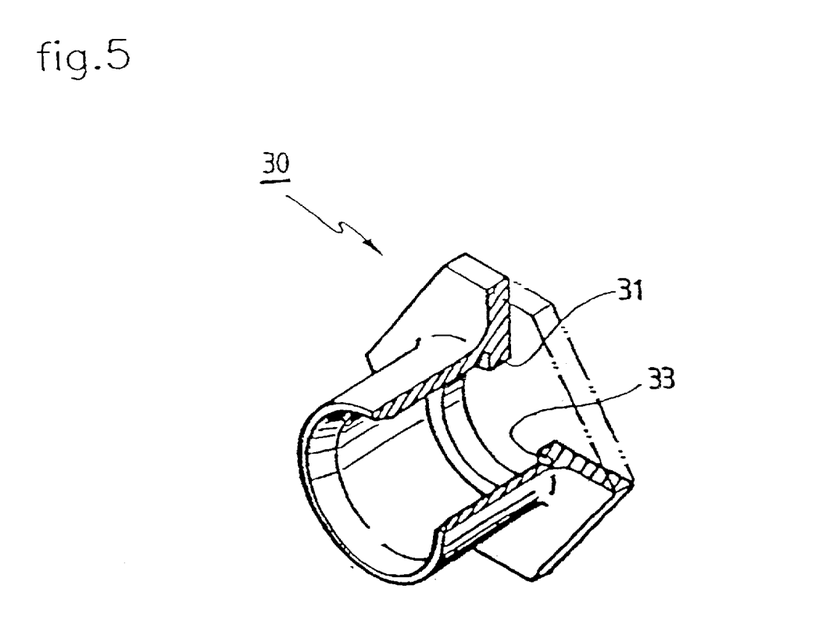
FIG. 5 is a perspective diagram showing a finger grip of this design.
Figure 6A:
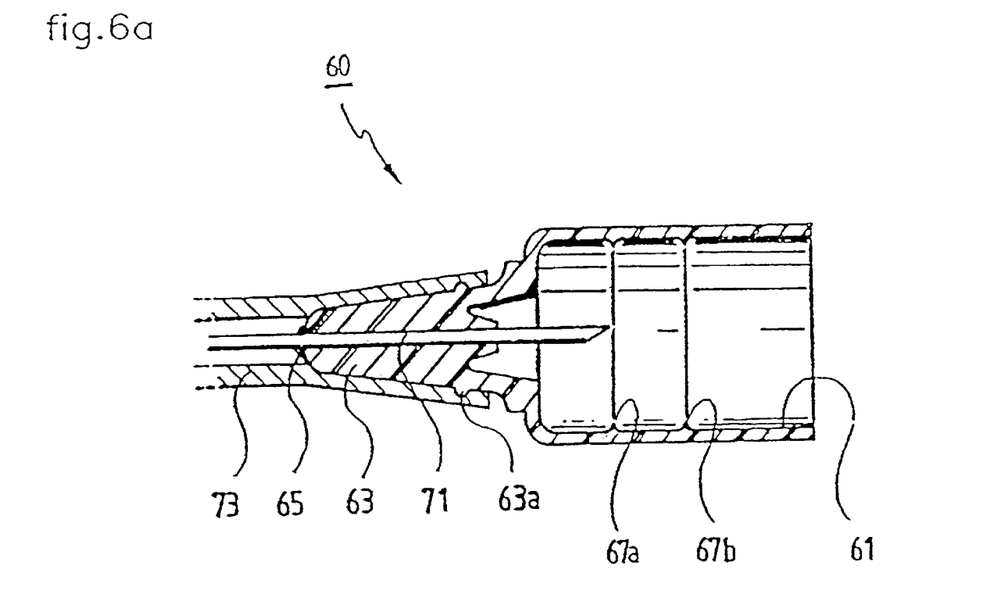
FIG. 6A is a cross-sectional view showing a needle hub of this design.
Figure 6B:
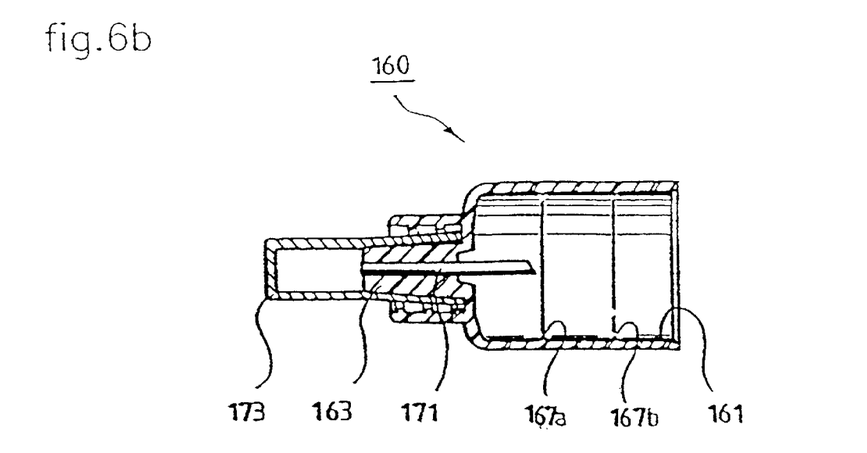
FIG. 6B is a cross-sectional view showing Luer lock needle hub of this design.
Figure 7:
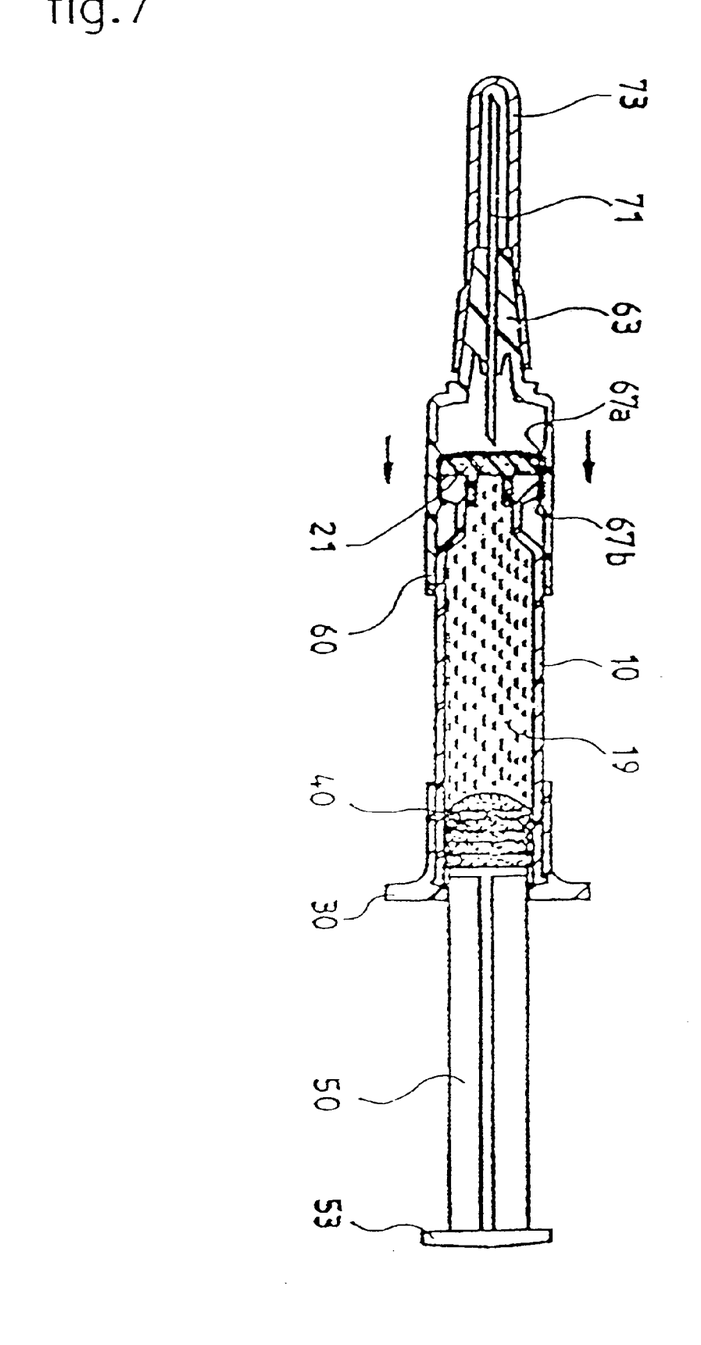
FIG. 7 is a diagram showing this design while not employed.
Figure 8:
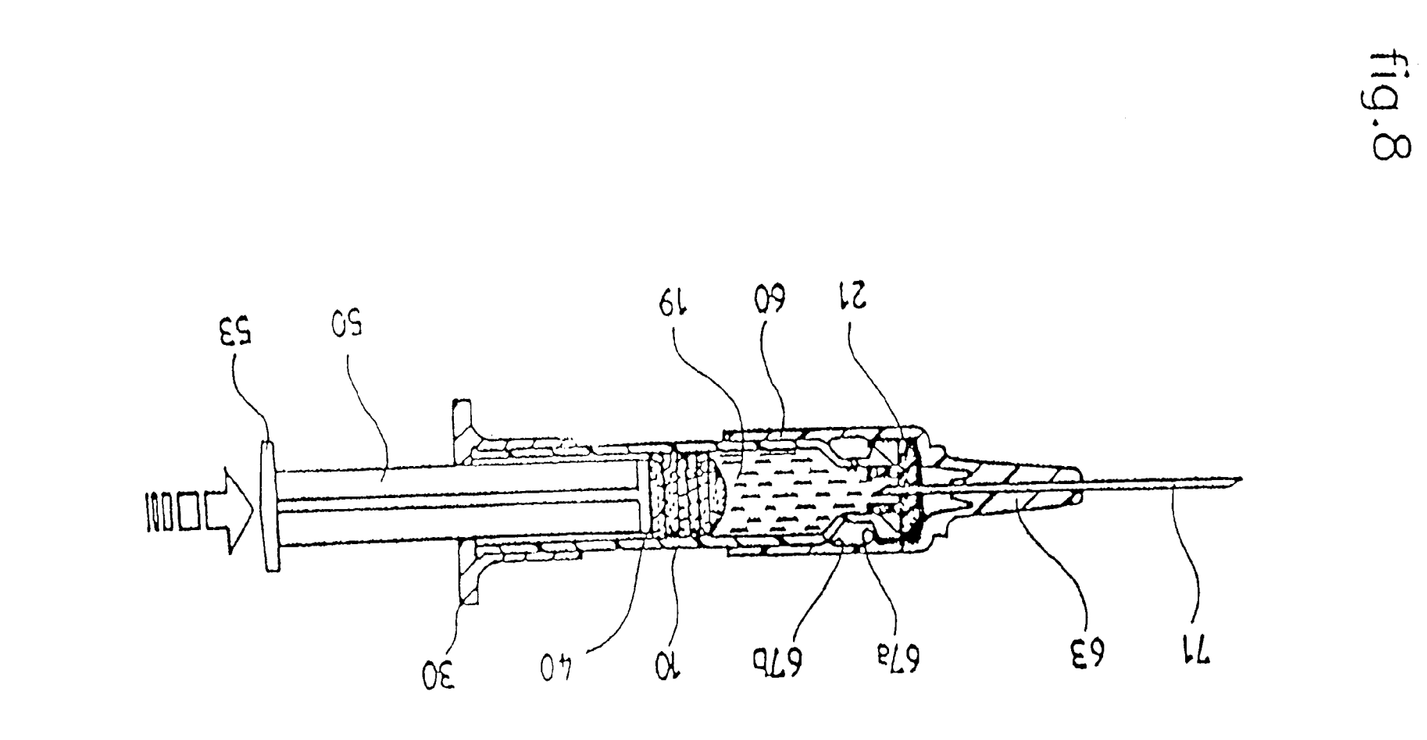
FIG. 8 is a diagram showing this design while in operation.

FIG. 1 is an elevational view of this design; FIG. 2 is a cross-sectional view of this design; FIG. 3 is a partial cross-sectional view of the glass tube sealed with aluminum cap of this design; FIG. 4 is a cross-sectional view where a plunger rod is mounted on a plunger tip of this design; FIG. 5 is a perspective diagram showing a finger grip of this design; FIG. 6A is a cross-sectional view showing a needle hub of this design; FIG. 6B is a cross-sectional view showing Luer lock needle hub of this design; FIG. 7 is a diagram showing this design while not employed; and FIG. 8 is a diagram showing this design while in operation.

First, referring to the drawings and particularly to FIGS. 1 through 6 thereof, there is illustrated one embodiment of a disposable syringe device in accordance with the invention which is generally designated by the reference number 100.

The syringe device 100 is adapted to be pre-filled with any suitable medicament which doctors, veterinarians, and other uses of syringes may wish to have readily available and store over a long period of time.

Devices filled with pharmaceutical materials in a ideally clean environment such as in a pharmaceutical laboratory cannot be duplicated in the field where pre-filled syringes are often needed.

Thus refilling the syringe assembly in the field presents additional risks to the patients and, accordingly, the unit is normally disposable.

The disposable syringe assembly 100 of the present design includes a glass tube 10 which has a finger grip 30 on one end and a needle hub 60 for mounting a needle on the other end.

The needle hub 60 has a similar shape of a needle 71 and can be replaced by a needle hub 160 having a similar length.

Also provided as a part of assembly is a hollow plunger 40 which has a plunger tip 41 at the terminal part.

As will be described hereinafter, the end of the glass tube 10 having the needle hub 60 is sealed prior to use.

The contents 19 are kept in the glass tube 10 by the plunger 40 which effectively seals the other end of the glass tube 10.

The plunger tip 41 formed at the end of the plunger 40 is mounted on a screw 51 of a plunger rod 50.

The plunger 40 is usually made from a particular formulation which the pharmaceutical manufacturer knows is compatible with the contents 19. A preferred material is manufactured from an extremely stable rubber.

The finger grip 30 is slidably mounted onto the outer diameter 17 of the glass tube 10 by a base which may also include a ring 31 to prevent movement of the finger grip 30 too far down the glass tube 10.

Also, the projection 17a is mounted at the end of the glass tube 10 to prevent the displacement of the finger grip 30 which is mounted on the glass tube 10. The projection 17a is mounted on a groove 33 which is formed in the finger grip 30 to prevent the displacement.

Further, at the opposite end of the finger grip 30 is a needle hub 60 which may mounted a needle hub 71.

The inner diameter 61 of the needle hub 60 has the same diameter as the outer diameter of the aluminum cap 25 for mounting the hub on the glass tube 10.

As will be described hereinafter, the aluminum cap 25 serves to protect the rubber seal 21 used for sealing one side of the glass tube.

The rubber seal 21 includes protruded support hump side 21b at the site inserted into the glass tube 10 and a round projection 21a at the contact site with the aluminum cap 2, being smaller than a hole 25a of the aluminum cap.

The outer diameter design of the glass tube 10 sealed by the rubber seal 21 and aluminum cap 25 is fabricated in such a manner that the diameters inserted into the needle hub 60 and finger grip 30 are same.

As shown in FIGS. 7 and 8, the needle assembly includes a double ended needle 71 which is held in place by a needle mount 63 and a sealing element 65.

An annular groove 73a of a needle shield 73 is held in place on a projection 63a of the needle mount 63.

The needle shield 73 serves to protect the needle prior to use.

The needle hub 60 also includes internal annular projections 67a, 67b which is positioned to hold the glass tube 10 during storage when the needle 71 is in a first position in axial alignment with the glass tube 10 but not penetrating the rubber seal 21 which is held by the aluminum cap 25 on the end of the glass tube 10.

As mentioned in the above, when the device is operational, the needle 73 is moved in the direction of arrow and penetrates the rubber seal which is held by the aluminum cap.

Hence, the lower part of the aluminum cap 25 is held by the first projection 67a of the needle hub 60 and the second projection 67b becomes positioned at the outer shoulder part of the glass tube 10.

When the syringe assembly is operational and with the finger grip 30 held in place, the disc 53 of the plunger rod 50 is pressed with a thumb, the plunger 40 is completely inserted into the glass tube 10 and all contents 19 within the glass tube 10 are discharged.

Hence, it is effective that the length of the plunger rod 50 is lower than that of the glass tube 10.

To discharge all contents within the glass tube 10, the end of the plunger 40 has an oval shape which is the same as the internal shoulder portion 15b of the glass tube 10.

Therefore, since the disposable syringe assembly having such structure decreases the volume of the finger grip to a great extent, this permits the volume during storage or transportation.

Since the finger grip has also a hexagonal shape, the device of this design has several advantages in that a) any part of syringe grip may be applicable prior to use, b) by preventing the displacement of a plunger before or after use, the discharge of contents during use or storage may be prevented, and c) the device cannot be refilled after use. Further, the device of this design is very useful in achieving the innate object of a disposable syringe assembly by solving the full administration of pharmaceuticals.

Further, by detachably mounting the rubber seal and aluminum cap, the device of this design can effectively prevent the mixing of aluminum particles into the medicaments.

As mentioned in the above, the principle of this design including structural details and many functional benefits are illustrated herein.

The use of the disposable syringe assembly according to this design may be understood by those having a common knowledge to which this design pertains. The reference numbers described in the main component of the following patent claim is not intended to limit the technological rights in such claims.

What is claimed is:

1. In a disposable syringe having a plunger having one end telescopically disposed in an open end of a glass tube for manually-activated axial movement toward an axially opposed sealed end of the glass tube and a hollow needle having one end disposed to rupture the sealed end to release through the needle an injectable composition contained in the glass tube, and a removeable needle shield covering the other end of the needle, the improvement comprising:

a seal element disposed on the one end of the plunger to force injectable composition toward the sealed end of the glass tube upon axial movement of the plunger;

a grip element fixed to the open end of the glass tube, the grip element including an outwardly-projecting annular flange disposed for manual gripping during use of the syringe and an inwardly-projecting annular flange disposed to engage the seal element and prevent removal of the plunger from the glass tube; and a needle hub having a needle mount at one axial end and a chamber open at the other axial end, the needle mount holding the needle to fix the one end thereof in a predetermined position in the chamber and the chamber being disposed to slidably, coaxially receive the sealed end of the glass tube, the chamber including two axially-spaced, generally parallel, annular projections disposed to engage the sealed end of the glass tube in spaced, axial relation to the one end of the needle and, upon use of the syringe, to permit relative axial movement of the tube toward the needle mount to rupture the seal with the one end of the needle, the needle hub being the sole structural connection between the needle and the glass tube.

2. The syringe of claim 1 wherein the seal element is coaxially threaded to the one end of the plunger.

3. The syringe of claim 1 wherein the glass tube includes an annular bead proximate the open end thereof and the grip element includes an annular groove disposed to engage the bead and fix the grip element to the open end of the glass tube.

4. The syringe of claim 1 wherein the seal element comprises an outer metal cap including an annular, axially extending skirt engaging the glass tube proximate the sealed end thereof and wherein the distance between the two annular projections is substantially equal to the axial length of the cap skirt.

* * * * *

UNITED STATES PATENT AND TRADEMARK OFFICE
CERTIFICATE OF CORRECTION

PATENT NO. : 6,352,522 B1
DATED : March 5, 2002
INVENTOR(S) : Han Wook Kim, Chung Sil Lee and Hyung Il Lee It is certified that error appears in the above-identified patent and that said Letters Patent is hereby corrected as shown below:

<u>Title page,</u>
Item [75], please change "Hyung Lee, II" to -- Hyung Il Lee --

Signed and Sealed this

Twenty-first Day of May, 2002

Attest:

*Attesting Officer*

JAMES E. ROGAN
*Director of the United States Patent and Trademark Office*